United States Patent
Tavares

(10) Patent No.: US 7,037,439 B2
(45) Date of Patent: May 2, 2006

(54) EMOLLIENT CARRIER GEL

(75) Inventor: Bruce Anthony Tavares, Hartland, WI (US)

(73) Assignee: React-NTI, LLC, Lino Lakes, MN (US)

( * ) Notice: Subject to any disclaimer, the term of this patent is extended or adjusted under 35 U.S.C. 154(b) by 156 days.

(21) Appl. No.: 10/661,656

(22) Filed: Sep. 12, 2003

(65) Prior Publication Data

US 2004/0054049 A1    Mar. 18, 2004

Related U.S. Application Data

(63) Continuation-in-part of application No. 10/436,555, filed on May 13, 2003, which is a continuation of application No. 10/126,414, filed on Apr. 19, 2002, now abandoned, which is a continuation-in-part of application No. 09/994,416, filed on Nov. 27, 2001, now abandoned.

(51) Int. Cl.
   *C09K 21/06*    (2006.01)
   *A61K 9/06*    (2006.01)

(52) U.S. Cl. .............................. 252/1; 424/63; 424/64; 424/78.03; 252/182.12; 252/363.5

(58) Field of Classification Search ........... 252/182.12, 252/1, 363.5; 424/63–64, 78.03; 524/474
See application file for complete search history.

(56) References Cited

U.S. PATENT DOCUMENTS

| | | | | |
|---|---|---|---|---|
| 1,831,544 A | * | 11/1931 | Pratt et al. | 516/47 |
| 3,086,909 A | * | 4/1963 | Kinzo et al. | 424/725 |
| 4,151,304 A | * | 4/1979 | Evans | 514/777 |
| 4,919,934 A | | 4/1990 | Deckner et al. | |
| 5,804,540 A | | 9/1998 | Tsaur et al. | |
| 6,036,945 A | * | 3/2000 | Deblasi et al. | 424/59 |
| 6,528,071 B1 | | 3/2003 | Vatter et al. | |

FOREIGN PATENT DOCUMENTS

| | | |
|---|---|---|
| EP | 0 519 727 A1 | 12/1992 |
| JP | 54-095723 * | 7/1979 |

* cited by examiner

*Primary Examiner*—Peter Szekely
(74) *Attorney, Agent, or Firm*—Alfred D. Lobo

(57) ABSTRACT

A waxy solid having ultrafine particles homogeneously distributed in a mixture of vegetable oil and waxy solid, the oil being present in a major proportion by weight, forms a homogeneous colloidal solution which is then cooled and subjected to high shear to form ultrafine particles of the waxy solid, in situ, in a size range from about 0.1 µm to 10 µm. The resulting stiff gel retains its shape and high viscosity for at least 30 days when confined in a container in an air atmosphere at 40° C. at substantially sea level. The stability of the gel is visually evidenced by a lack of syneresis. The gel is destabilized at a temperature in the range from 52° C. (125° F.) to 100° C. (212° F.).

10 Claims, No Drawings

EMOLLIENT CARRIER GEL

CROSS REFERENCE TO RELATED APPLICATIONS

This application is a continuation-in-part of copending application Ser. No. 10/436,555 filed May 13, 2003, which is a continuation of copending application Ser. No.10/126,414 filed Apr. 19, 2002 now abandoned, which is a continuation-in-part application of Ser. No. 09/994,416 filed Nov. 27, 2001, now abandoned.

FIELD OF THE INVENTION

This invention relates to a novel carrier in the form of a gel (hence also referred to as a "carrier gel") for use in a cosmetic composition which can be applied topically to the human body surface, especially the skin (including the mucosae), hair and nails.

THE PROBLEM

A carrier is sought which will provide physical properties comparable to those of petrolatum in cosmetic compositions, particularly the viscosity, stability, emolliency and occlusivity of petrolatum, without being burdened with the objectionable properties of petrolatum. More particularly, the carrier is required to (i) have a naturally occurring vegetable oil as a major component by weight and be substantially free of any pigment, solvent including water, or surfactant, and (ii) incorporate up to 15% by weight of an inert micron-sized solid which has no cosmetic function, as does a pigment, without being destabilized at 40° C.

BACKGROUND OF THE INVENTION

The present invention relates to an emollient gel useful as a carrier for essential ingredients of a cosmetic composition. The carrier may be used as a substitute for petrolatum (also known as petroleum jelly or soft paraffin obtained from petroleum), which is a colorless to amber gelatinous semi-solid consisting of various alkane and olefin hydrocarbons. When applied to the body, petrolatum provides an occlusive film which minimizes loss of water from tissues underlying the surface of the body into the environment; the water is thus accumulated in the stratum corneum. However, the novel carrier, despite being formulated with a substantial amount of wax or waxy solid, does not have a sticky, greasy, or waxy feel, among other undesirable sensory and aesthetic properties which are well known to be defining characteristics of petrolatum. In view of these negative attributes of petrolatum, attempts to provide an acceptable substitute essentially free of petrolatum's drawbacks, have intensified.

The term "waxy solid" is used hereinafter to denote both, a wax which is (i) an ester of at least one higher monohydric aliphatic or phytosterol alcohol with a high molecular weight fatty acid, and also (ii) a material which is not a "fat" and does not have the foregoing chemical structure of a wax, but has the physical attributes of wax. By "fat" is meant a mixed glyceryl ester of higher "fatty" acids such as stearic, palmitic and oleic acids, or any mixture of such glyceryl esters. Waxes are distinguished from fats in that they are esters of monohydric alcohols. Waxes used in this invention are commercially available in slabs, pellet, prill or powder form, the last form having the smallest particle size typically greater than 45 μm (micrometers) or 325 mesh Standard Test Sieves (wire cloth). Examples of waxy solids are polyglycol waxes such as polyethylene oxide and polypropylene oxide waxes, ethylene-vinyl acetate copolymers, and oxidized polyolefin homopolymers such as oxidized polyethylene wax, each formulated with a molecular weight to mimic a wax which is a solid at 40° C.

The carrier gel is a colloid in which the dispersed phase of waxy solid particles has combined with the continuous phase of vegetable oil to produce a semi-solid material.

SUMMARY OF THE INVENTION

It has been discovered that by providing a waxy solid having ultrafine particles homogeneously distributed in a mixture in which a naturally occurring vegetable oil is present in a major proportion by weight, and the waxy solid is present in a minor proportion by weight, to form a homogeneous colloidal solution which is then cooled and subjected to high shear to form the ultrafine particles of the waxy solid in situ, a stiff gel is obtained which retains its shape and high viscosity for at least 30 days when confined in a container in an air atmosphere at 40° C. at substantially sea level. The stability of the gel is visually evidenced by a lack of syneresis.

The carrier gel is an essentially anhydrous, hydrophobic, substantially pigment free, homogeneous and stable gel, free of synthetic oils, consisting essentially of a minor proportion by weight of a waxy solid and a major proportion by weight of a naturally occurring vegetable oil which oil may include from 0 to 15% by weight of a hydrogenated vegetable oil. Ultrafine particles of waxy solid, preferably present in an amount in the range from at least 5% to 35% by weight and in a size range from about 0.1 μm to 10 μm, preferably 0.1 μm to 5 μm, provide the surface area which appears to be essential to impart the necessary high viscosity to the carrier gel, as well as its high stability as evidenced by its destabilization point in the range from 52° C. (125° F.) to 100° C. (212° F.). The viscosity of the carrier gel is measured with a Brookfield Model DV-II+ Viscometer on a Model D Helipath stand, using T-bar spindles ranging from "T-A" to "T-F", each T-bar graded to measure a successively higher step-increment in viscosity. The viscosities of the carrier gel so measured are in the range from about 10,000 cP at 25° C. measured with a T-A bar at 0.5 rpm, to about 100,000 cP at 25° C. measured with a T-F bar at 0.1 rpm. By substantially pigment-free is meant that there is less than 10%, preferably less than 5% by weight of pigment, and most preferably no pigment, color typically being provided by a dye or non-solid coloring agent. By "stable" is meant that the gel retains its physical properties for at least 30 days when confined in a container in an air atmosphere at 40° C. at substantially sea level. The gel is used as a carrier for cosmetically active ingredients including vitamins, minerals, skin conditioning agents, colorants, fragrances, and the like depending on the desired end use of the cosmetic; and as a carrier for ultrafine particles of cotton fibers having an average particle size smaller than 10 μm present in a minor amount by weight.

The carrier gel is produced in a two-stage process. In a first stage, by heating a mixture of vegetable oil and waxy solid components to a temperature above the melting point of the waxy solid but below a temperature at which either of the components is degraded, preferably from about 5° C. to 20° C. above the melting point of the waxy solid, to form a colloidal solution; and, cooling the mixture to a temperature below about 38° C. (100° F.) to form a slurry having an initial viscosity in the range from about 2,000 cP to 50,000 cP at 25° C. In the second stage, by mixing the cool slurry with sufficient energy to generate the ultrafine particles and raise the temperature at least 5° C. to form a rheopectic mass and simultaneously cooling the mass to keep the temperature below 49° C. (120° F.); and thereafter further cooling the warm gel to obtain a stable emollient carrier gel having viscosity in the range from 10,000 cP at 25° C. measured with a T-A bar at 0.5 rpm, to about 100,000 cP at 25° C. measured with a T-F bar at 0.1 rpm, each measured with a Brookfield Model DV-II+ Viscometer on a Model D Helipath stand. It is essential that the mixture be subjected to such high shear energy substantially continuously, in order to obtain a gel which has essentially no visible slump, that is, the gel is stiff enough to allow a mounded mass of the gel placed on a flat surface to maintain its mounded shape for at least 24 hr at 30° C. It is desirable to keep the gel, soon after it is formed, open to an air atmosphere to allow the gel to be tempered; a drum of the gel, if sealed immediately after the gel is subjected to high shear, tends to be destabilized; if sealed after about 8 hr, the stability is maintained.

DETAILED DESCRIPTION OF PREFERRED EMBODIMENTS

The carrier gel is typically composed of at least one waxy solid and at least one vegetable oil, and is required to have physical properties similar to those of petrolatum so that the gel may be used in cosmetic compositions which might use petrolatum. Thus the physical properties of the gel are such that it is stiffer or harder than shaving cream which temporarily retains its shape, but not as stiff as a deodorant bar; its drop point cannot be measured because the gel will not flow through a tube unless heated sufficiently to destabilize the gel; an attempt to measure viscosity after liquefying the gel is not indicative of its viscosity before it was liquefied; moreover, once liquefied, the gel cannot return to its original gel form. Therefore viscosity is measured with a Brookfield viscometer using the aforementioned T-bars. Hereafter, for brevity and convenience, reference to "oil" means "vegetable oil" unless stated otherwise.

The oil, or a blend of oils, which may be present in an amount in the range from about 55% to 95% by weight, is typically present in the range from about 60% to 90%, and most preferably from about 70% to 80%. The waxy solid, or a blend of wax(es) and waxy solids, which may be present in an amount in the range from about 5% to 40% by weight, is typically present in the range from about 5% to 35%, and most preferably from about 10% to 25%. Preferred commercially available natural and synthetic waxy solids are deodorized and purified to remove impurities and have a melting point in the range from about 40° C. to 200° C., preferably from 60° C. to 180° C.

It is essential that the waxy solid be present in the dispersed phase of the gel in ultrafine particulate form. To ensure an average particle size smaller than 10 μm in the gel, the waxy solid is melted in the vegetable oil to form a colloidal solution. It is critical that the colloidal solution be then cooled to a temperature below 38° C. (100° F.) before being further homogenized in a high-shear mixture to form the gel, and that the resulting gel be cooled while in the colloid mill or homogenizer so that the temperature does not rise above 49° C. (120° F.). Without cooling the gel being formed in the colloid mill, sufficient energy due to high-shear mixing is expended in the gel to raise its temperature at least 20° C. (68° F.) above the initial temperature at which the colloidal solution is charged to the mill. The energy dissipated in the colloidal solution (as it becomes rheopectic) appears to enhance the attraction between the waxy particles in the dispersed phase and the dispersion medium of oil. However, exceeding the 49° C. temperature of the gel appears to destabilize the gel.

Mixing finely divided particles of the waxy solid, smaller than 10 μm (e.g. particles of Acumist A-12 oxidized polyethylene homopolymer obtained from Honeywell) into oil at a temperature below the melting point of the waxy solid, then subjecting the mixture to the same amount of energy in the same high-shear mixing equipment as used for the colloidal solution while not allowing the temperature to rise to 49° C., fails to form a gel having the same hardness (ASTM D-5) or stiffness (as yield point measured by a penetrometer) as one formed from a colloidal solution, which, when the gel is formed, is rapidly cooled to below 49° C. (120° F.) about 38° C. (100° F.). It appears that rapidly cooling the gel "sets" or "freezes" the size of the micron-sized particles in the dispersed phase, and it is the presence of such particles which appears to be critical to formation of the gel.

As will be expected, the rate of cooling will vary depending upon the particular components chosen, the relative proportion of each, the temperature to which the gel formed is allowed to rise, the rate at which heat is removed from the gel (which is a function of the type of heat exchange equipment used), the desired final hardness or stiffness (measured as yield point by a penetrometer) of the gel formed, and other defining characteristics of the gel. In general, the faster the entire gel is cooled, the better.

The Vegetable Oil:

The oil may only be obtained from a naturally occurring source for a vegetable oil. Commonly available oils include macadamia oil, palm oil, coconut oil, wheat germ oil, avocado oil, almond oil, sunflower oil, safflower oil, canola oil, soybean oil. Still other oils are sunflower seed oil, canola or rapeseed oil, castor oil, meadowform seed oil, jojoba oil, corn oil, olive oil, peanut oil, sesame oil, coconut oil, soybean oil, macadamia oil, babassu oil, squalame oil, safflower oil, apricot kernel oil, almond oil, avocado oil, rice bran oil, wheat germ oil, grape seed oil, borage oil and evening primrose oil. The less stable oils listed can be used, but as noted are preferably stabilized with respect to oxidation. Since oils with a higher degree of unsaturation tend to be less stable when exposed to the atmosphere, typically due to oxidation, the choice of oil, or a blend of oils, in a gel will depend upon the degree of stability sought in the gel; in general, the higher the oleic acid content of an oil the more stable is the gel formed because low oleic acid content oils have relatively high amounts of acids with higher unsaturation. Susceptibility to oxidation is decreased by hydrogenation but the effect of the changed properties of the hydrogenated oil must be compensated in the gel. Preferred natural oils are deodorized and purified to remove contaminant proteins and have a viscosity in the range from about 20 cP to 50 cP at 40° C. The oleic acid content of "low" oleic acid oils is in the range from about 5–23%; and of a "high" oleic acid oil is in the range from about 45–85%. An examples of a low oleic acid content oil is soya oil; examples of high oleic acid content oils are canola oil and safflower oil.

The Waxy Solid:

Oxidized waxes used have an average molecular weight (Mw) of from about 700 to about 10,000, preferably from about 1,500 to about 5,000 and are commercially available. The melting point of oxidized waxes used ranges from about 70° C. (158° F.) to about 200° C. (392° F.) while the destabilization point of the emollient gel composition itself typically ranges from about 52° C. (125° F.) to about 150°

C. (302° F.). An oxidized polyolefin wax may have an acid value of from about 10 to 45, preferably from about 15 to 40, and most preferably from 15 to 30. A description of suitable oxidized polyolefin waxes is found in German patent application Nos. 2035706, 3047915 and 2201862. Preferred oxidized waxes are oxidized microcrystalline wax, oxidized Fischer Tropsch waxes, oxidized polyethylene waxes and oxidized polypropylene waxes.

Other preferred waxes are microcrystalline wax, beeswax, candililla wax, berry wax, montan wax, polyethylene wax and ethylene vinyl acetate (EVA) copolymers. A preferred microcrystalline wax has a molecular weight in the range from 100 to 1000. The choice of oil depends on the end use, some oils having higher lubricity, others having higher resistance to oxidation and thermal breakdown. Upon selection of the oil a waxy solid is selected and added to the oil, the amount of wax added influencing the viscosity and melt point of the gel to be formed.

The following are illustrative carrier gels prepared from only an oil and a waxy solid present in the weight ratios given below:

| Carrier Gel 1: | |
| --- | --- |
| Soya oil | 70% |
| Microcrystalline wax* | 30% |
| Carrier Gel 2: | |
| Canola oil | 58% |
| Soya oil | 20% |
| Hydrogenated soya oil | 15% |
| Candelilla wax | 7% |
| Carrier Gel 3: | |
| Canola oil | 55% |
| Soya oil | 15% |
| Hydrogenated soya oil | 15% |
| Berry wax | 15% |
| Carrier Gel 4: | |
| Canola oil | 58% |
| Soya oil | 16% |
| Safflower oil | 7% |
| EVA copolymer (AC 400) | 19% |
| Carrier Gel 5: | |
| Canola oil | 57% |
| Soya oil | 13% |
| Hydrogenated soya oil | 15% |
| Beeswax | 15% |
| Carrier Gel 6: | |
| Soya oil | 75% |
| Hydrogenated soya oil | 15% |
| Microcrystalline wax* | 10% |

*Astorwax 3040 obtained from Honeywell Int'l.

In each of the foregoing examples, the following procedure, illustrated with specific components and amounts, was used:

| | | |
| --- | --- | --- |
| Canola oil | 1160 g | 58% |
| Soya oil | 320 g | 16% |
| Safflower oil | 140 g | 7% |
| EVA (A-C 400) | 380 g | 19% |
| Total | 2000 g | 100% |

The gel is made in a two-stage process: First, the oils at ambient temperature 25.2° C. (77.5° F.) are charged into a large pyrex beaker and the mixture heated on a hot plate. When the temperature of the mixture rose to 82° C. (180° F.) the EVA was gradually added while mixing with a hand-held propeller mixer which was inserted in the mixture to churn it sufficiently to form a colloidal solution. The mixture was initially cloudy but upon heating to 99.5° C. (211° F.) became a clear colloidal solution. The mixture was then cooled in ice water to room temperature (25° C.). In the second stage, the beaker holding the cooled colloidal solution was placed in a cooling water bath with the dispersing blade of a homogenizer inserted in the colloidal solution. The homogenizer used a Balder Electric Co. electric motor rated to draw 7 amps with 115 volt current, which motor was drivingly connected to a shaft having at its end a Greereo Model IL dispersing blade (serial number 3-02827B). The homogenizer was run by controlling it with a rheostat so that the temperature of the gel being formed in the beaker rose about 13° C. to 38° C., but was not allowed to rise above 49° C. (120° F.), enough cooling water being used to keep the temperature at about 38° C. (100° F.). The gel formed was firm but easily removed from the beaker with a spatula. The gel so removed was held in a large jar, open to the atmosphere, at room temperature, for 8 hr before the jar was sealed.

A sample of the gel was drawn down on a NPIRI grind gauge which indicated that there were no waxy particles greater than 10 μm present.

On a larger scale it is desirable, in the first stage, to make the slurry in a conventional jacketed tank equipped with a relatively high-shear mixer to make the colloidal solution, first by heating the tank with Dowtherm to above the melting point of the waxy solids added while stirring, then substituting ice-cold fluid for the Dowtherm in the jacket to chill the slurry rapidly. In the second stage, the cooled slurry is pumped to a jacketed heat-exchanger equipped with a high-shear mixer having blades for scraping the walls of the heat exchanger. Such a device, commercially referred to as a high-shear votator, dissipates enough energy to continuously form a stiff gel which under the relatively elevated temperature, about 43° C. (110° C.) of the votator, allows the gel to be pumped into receiving drums where it is cooled further.

Having thus provided a general discussion, described the carrier gel produced and the process for making it, in detail, and illustrated the invention with specific examples of the best mode of carrying it out, it will be evident that the invention has provided an effective solution to a long-standing problem. It is therefore to be understood that no undue restrictions are to be imposed by reason of the specific embodiments illustrated and discussed, and particularly that the invention is not restricted to a slavish adherence to the details set forth herein.

What is claimed is:

1. An essentially anhydrous, hydrophobic, substantially pigment free, homogeneous and stable carrier gel, free of synthetic oils, consisting of a minor proportion by weight of a waxy solid and a major proportion by weight of a naturally occurring vegetable oil, the gel being present as a colloid in which the dispersed phase of waxy solid particles has combined with the continuous phase of vegetable oil to produce a semi-solid material substantially free of any solvent, the gel having physical properties including viscosity, stability, emolliency and occlusivity similar to that of petrolatum so as to be a substitute for petrolatum but having a destabilization point in the range from 520° C. (125° F.) to 100° C. (212° F.).

2. The carrier gel of claim 1 wherein the vegetable oil includes from 0 to 15% by weight of a hydrogenated vegetable oil and the gel has particles of waxy solid in a size range from about 0.1 μm to 10 μm homogeneously distributed as a disperse phase the gel having a viscosity in the range from 10,000 cP at 25° C. measured with a T-A bar at 0.5 rpm. to about 100,000 cp at 25° C. measured with a T-F bar at 0.1 rpm. each measured with a Brookfield Model DV-II+ Viscometer on a Model D Helipath stand, the gel being stable for at least 30 days when confined in a container in an air atmosphere at 40° C. at substantially sea level.

3. The carrier gel of claim 1 wherein the vegetable oil is present in an amount in the range from about 55% to 95%, and the waxy solid is present in an amount in the range from about 5% to 40%.

4. The carrier gel of claim 3 wherein the vegetable oil is present in an amount in the range from about 60% to 90% by weight of the gel, and the waxy solid is present in an amount in the range from about 10% to 25%.

5. A method for preparing a carrier gel, comprising,
heating a mixture consisting of a minor proportion by weight of a waxy solid and a major proportion by weight of a vegetable oil substantially free of any solvent, to a temperature above the melting point of the waxy solid but below a temperature at which either of the components is degraded to form a homogeneous colloidal solution;
cooling the mixture to a temperature below about 38° C. (100° F.) to form a slurry having an initial viscosity in the range from about 2,000 cp to 50,000 cp at 25° C.; continuously mixing the slurry with sufficient energy to raise the temperature at least 5° C. to form a rheopectic mass and simultaneously cooling the mass to a temperature below 49° C. (120° F.);
thereafter cooling the rheopectic mass to ambient temperature; and,
recovering a cool and stable carrier gel having physical properties similar to that of petrolatum so as to be a substitute for petrolatum but having a destabilization point in the range from 52° C. (125° F.) to 100° C. (212° F.).

6. The method of claim 4 wherein the cool gel having no visible slump at 30° C. for a period of 24 hr, and a viscosity in the range from 10.000 cP at 25° C. measured with a T-A bar at 0.5 rpm, to about 100,000 cP at 25° C. measured with a T-F bar at 0.1 rpm, each measured with a Brookfield Model DV-II+ Viscometer on a Model D Helipath stand is held open to the atmosphere for at least 8 hr to enhance the stability of the gel.

7. The method of claim 4 including heating the mixture to a temperature from about 5° C. to 20° C. above the melting point of the waxy solid; and, wherein the vegetable oil is present in an amount in the range from about 55% to 95%, and the waxy solid is present in an amount in the range from about 5% to 45%.

8. An emollient carrier gel produced by heating a mixture consisting of a minor proportion by weight of a waxy solid and a major proportion by weight of a naturally occurring vegetable oil substantially free of any solvent, to a temperature above the melting point of the waxy solid but below a temperature at which either of the components is degraded to form a homogeneous colloidal solution;
cooling the mixture to a temperature below about 38° C. (100° F.) to form a slurry having an initial viscosity in the range from about 2,000 cp to 50,000 cp at 25° C.; continuously mixing the slurry with sufficient energy to raise the temperature at least 5° C. to form a rheopectic mass and simultaneously cooling the mass to a temperature below 49° C. (120° F.);
thereafter cooling the rheopectic mass to ambient temperature; and, recovering a cool and stable carrier gel having physical properties similar to that of petrolatum so as to be a substitute for petrolatum but having a destabilization point in the range from 52° C. (125° F.) to 100° C. (212° F.).

9. The carrier gel of claim 7 wherein the cool and stable gel is held open to the atmosphere for at least 8 hr to enhance the stability of the gel.

10. The carrier gel of claim 7 including heating the mixture to a temperature from about 5° C. to 20° C. above the melting point of the waxy solid; and, wherein the vegetable oil is present in an amount in the range from about 55% to 95%, and the waxy solid is present in an amount in the range from about 5% to 45%.

* * * * *